(12) United States Patent
Banno et al.

(10) Patent No.: US 6,886,412 B2
(45) Date of Patent: *May 3, 2005

(54) ULTRASONIC-WAVE PROPAGATION-TIME MEASURING METHOD AND GAS CONCENTRATION SENSOR

(75) Inventors: Keigo Banno, Aichi (JP); Hideki Ishikawa, Aichi (JP); Yoshikuni Sato, Aichi (JP); Noboru Ishida, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/076,423

(22) Filed: Feb. 19, 2002

(65) Prior Publication Data

US 2002/0117003 A1 Aug. 29, 2002

(30) Foreign Application Priority Data

Feb. 19, 2001 (JP) ........................................ 2001-041680

(51) Int. Cl.⁷ ............................ G01F 1/66; G01N 29/02
(52) U.S. Cl. .................................. 73/861.27; 73/24.01
(58) Field of Search ................................ 73/24.01, 597, 73/598, 596, 602, 861.25, 861.27, 861.29, 861.28, 861.31, 302; 702/190

(56) References Cited

U.S. PATENT DOCUMENTS

| 4,022,058 | A | * | 5/1977 | Brown | ........................ 73/560 |
|---|---|---|---|---|---|
| 4,515,021 | A | | 5/1985 | Wallace et al. | |
| 4,538,469 | A | | 9/1985 | Lynnworth et al. | |
| 6,418,782 | B1 | * | 7/2002 | Sato et al. | .................. 73/24.01 |
| 6,568,240 | B1 | * | 5/2003 | Sato et al. | .................... 73/1.07 |
| 6,568,281 | B1 | * | 5/2003 | Sato et al. | ............... 73/861.27 |

FOREIGN PATENT DOCUMENTS

| EP | 1077365 | * | 2/2001 |
|---|---|---|---|
| JP | 60-502171 | | 12/1985 |
| JP | 5-72527 | | 10/1993 |
| JP | 9-318644 | * | 12/1997 |

* cited by examiner

Primary Examiner—Helen C. Kwok
(74) Attorney, Agent, or Firm—Sughrue Mion, PLLC

(57) ABSTRACT

An ultrasonic-wave propagation-time measuring method and gas concentration sensor are disclosed in which a reception wave which has been transmitted and received by an ultrasonic element 5 is subjected to full-wave rectification in order to obtain a full-wave-rectified wave, which is then integrated by an integration circuit 37 to obtain an integral value. A peak value of the integral value is held by a peak-hold circuit 39. As to detection of gas concentration, a threshold-level calculation section 21e sets a reference value on the basis of the peak value, and a point in time when the amplitude of a reception wave having undergone full-wave rectification is judged by a comparator 43 to have reached the reference value is regarded as an arrival time. Subsequently, a gas concentration is determined on the basis of a period between the emission time and the arrival time.

9 Claims, 9 Drawing Sheets

ULTRASONIC-WAVE PROPAGATION-TIME MEASURING METHOD AND GAS CONCENTRATION SENSOR

BACKGROUND OF THE INVENTION

1. Field of the Invention

The present invention relates to an ultrasonic-wave propagation-time measuring method and to a gas concentration sensor.

2. Description of the Related Art

Techniques for measuring sound velocity on the basis of propagation time of ultrasonic waves have been proposed in, for example, Japanese Patent Publication (kokoku) No. 5-72527 and Japanese Kohyo (PCT) Patent Publication No. 60-502171.

In these techniques, an ultrasonic element is caused to transmit an ultrasonic wave (transmission wave) and receive its reflection wave (reception wave); and sound velocity is measured on the basis of the propagation time between transmission of the transmission wave and reception of the reception wave.

In a well-known method of measuring propagation time, more particularly, with regard to detecting the reception signal, a threshold level (reference value) of a comparator is fixed, and the reception wave itself or an integral value of the reception wave is compared with the fixed threshold level.

However, ultrasonic reception waves sometimes attenuate due to pressure or other causes. In such a case, the conventional techniques use a fixed value for the threshold level of the comparator, a measured propagation time includes an error stemming from attenuation of the reception wave.

Thus, in some cases a sound velocity calculated from the propagation time may become inaccurate.

SUMMARY OF THE INVENTION

The present invention has been devised in order to solve the above problems, and an object of the invention is to provide an ultrasonic-wave propagation-time measuring method and a gas concentration sensor which enable accurate determination of propagation time.

(1) To achieve the above object, the invention provides an ultrasonic-wave propagation-time measuring method in which an ultrasonic wave is transmitted by use of an ultrasonic element, a reflection wave of the transmission wave is received as a reception wave by use of the same ultrasonic element or a different ultrasonic element, and a period of time between transmission of the ultrasonic wave and reception of the reception wave is measured as a propagation time, the method being characterized by comprising: a reference-value setting step of subjecting a reception wave to full-wave rectification to obtain a full-wave-rectified wave, integrating the full-wave-rectified wave or a portion thereof in order to obtain an integral value, and setting a reference value on the basis of the integral value; and a propagation time measurement step of determining an arrival time of the reception wave by use of the reference value when the propagation time is measured.

In the present invention, an ultrasonic reception wave is subjected to full-wave rectification in order to obtain a full-wave-rectified wave, and a reference value (a threshold level) is set on the basis of the full-wave-rectified wave. At the time of actual measurement of propagation time, a reception wave or a full-wave-rectified wave obtained therefrom is compared with the reference value using, for example, a comparator; and a time at which the comparator generates a first one of a series of pulses (when the amplitude of the reception wave or full-wave-rectified wave exceeds the reference value) is detected as an arrival time of the reception wave.

That is, ultrasonic reception waves sometimes attenuate due to the surrounding atmosphere (e.g., atmospheric pressure). In such a case, when a fixed reference value is used as in the conventional techniques, the time which a reception wave or full-wave-rectified wave requires to reach a fixed value increases, making accurate measurement of propagation time impossible. Therefore, in the present invention, the reference value is adjustably set on the basis of the strength of the reception signal.

Accordingly, when a reception wave attenuates, the reference value (which is set on the basis of the reception wave or a full-wave-rectified wave obtained therefrom) also decreases. Therefore, at the time of actual measurement, the point in time when a reception wave or full-wave-rectified wave attains the (lowered) reference value represents an accurate arrival time. In other words, in the present invention, the reference value itself can be adjusted in consideration of pressure and other factors which influence propagation time. Therefore, even when a reception wave attenuates due to pressure or other cause during actual measurement, the propagation time between transmission of the transmission wave and reception of the reception wave does not change, so that accurate measurement of propagation time can be effected at all times.

Moreover, in the present invention, since full-wave rectification is employed in the reference-value setting step, the reference value follows attenuation of a reception wave at higher speed as compared with the case in which a reception wave not having been subjected to full-wave rectification is used.

This feature will be described with reference to FIGS. 1 and 2. FIG. 1 shows in its upper section a full-wave-rectified wave, and in its lower section rectangular waves which are generated from the full-wave-rectified wave as will be described below. FIG. 2 shows in its upper section a reception wave, and in its lower section rectangular waves corresponding to the reception wave. In FIGS. 1 and 2, the waves are arranged in accordance with the degree of attenuation such that the degree of attenuation increases toward the right.

As exemplified in FIG. 1, the integration in the reference-value setting step is performed by the steps of comparing a full-wave-rectified wave (upper section of FIG. 1) with a predetermined value a, generating rectangular waves (lower section of FIG. 1) which correspond to the number of pulses having amplitudes greater than the predetermined value a, and integrating the rectangular waves.

When this integration method is employed, as the degree of attenuation of the full-wave-rectified wave increases (from (1) to (4)), the number of pulses having amplitudes greater than the predetermined value a (i.e., the number of rectangular waves) decreases, a smaller value is calculated as an integral value, and a smaller value is set as a reference value.

In the present invention, since a full-wave-rectified wave, which includes a greater number of pulses in total, is used as a wave to be compared with the predetermined value a, as illustrated in FIG. 1, the number of rectangular waves decreases to accurately follow attenuation of the full-wave-rectified wave (i.e., there is not a case in which the number of rectangular waves does not decrease in spite of attenuation of the full-wave-rectified wave or the number of rectangular waves decreases greatly in response to slight attenuation of the full-wave-rectified wave).

By contrast, in the case in which a reception wave not having undergone full-wave rectification is used as a wave to be compared with the predetermined value a, as illustrated in (1) of FIG. 2, the number of rectangular waves fails to decrease to accurately follow attenuation of the full-wave-rectified wave, because of a smaller number of pulses included in the reception wave (half the number of pulses included in the full-wave-rectified wave).

In other words, a problem arises in that the number of rectangular waves does not change in spite of attenuation of the reception wave (from (2) to (3) in FIG. 2), or the number of rectangular waves decreases greatly in response to slight attenuation of the reception wave (from (3) to (4) in FIG. 2).

As described above, in the present invention, the number of rectangular waves decreases to accurately follow attenuation of a reception wave, and therefore, the reference value (which is set on the basis of an integral value of the rectangular waves) also decreases to accurately follow attenuation of the reception wave.

As a result, the ultrasonic-wave propagation-time measuring method according to the present invention enables accurate measurement of propagation time, while further eliminating the influence of variation in atmospheric pressure and other factors.

In the reference-value setting step, through use of, for example, a microcomputer, the reference value is obtained through a calculation of multiplying the integral value by a predetermined coefficient.

The predetermined coefficient may be changed in accordance with the integral value.

The term "full-wave-rectified wave" refers to a wave obtained through full-wave rectification of a reception wave.

(2) Preferably, the invention is further characterized in that in the propagation time measurement step, a point in time when the reception wave or the full-wave-rectified wave has reached the reference value is measured as an arrival time.

In the propagation time measurement step of the ultrasonic-wave propagation-time measuring method according to the present invention, a point in time when (the amplitude) of a reception wave or full-wave-rectified wave has reached the reference value is measured as an arrival time.

Therefore, the present invention can eliminate the necessity of integrating reception waves, which is required in a method in which a reception wave is integrated to obtain an integral value, and a point in time when the integral value has reached the reference value is measured as an arrival time. Thus, calculation processing and apparatus configuration can be simplified.

(3) Optionally, the invention is further characterized in that in the propagation time measurement step, the reception wave or full-wave-rectified wave or a portion thereof is integrated to obtain an integral value, and a point in time when the integration value has reached the reference value is measured as an arrival time.

In the ultrasonic-wave propagation-time measuring method according to the present invention, a point in time when an integral value obtained through integration of the reception wave, a portion of the reception wave, the full-wave-rectified wave, or a portion of the full-wave-rectified wave has reached the reference value is measured as an arrival time.

In the present invention, since an integral value obtained through integration of, for example, the reception wave is used for determining the arrival time, even when the reception wave or full-wave-rectified wave contains noise, the noise does not cause erroneous determination of the arrival time.

In other words, since noise contained in a portion of the reception wave or full-wave-rectified wave hardly affects the integral value, the arrival time is not influenced by noise.

(4) A further aspect of the invention provides a gas concentration sensor which utilizes the ultrasonic-wave propagation-time measuring method of the invention, in any form as described above.

Propagation time of an ultrasonic wave varies depending on the concentration of a specific gas (e.g., vaporized fuel) to be detected, which is contained in a gas under measurement (e.g., atmospheric gas such as air). Therefore, the concentration of the specific gas can be detected by measuring the propagation time of ultrasonic waves.

In particular, in the present invention, since propagation time can be measured accurately by use of the above-described ultrasonic-wave propagation-time measurement method, gas concentration can be detected accurately.

(5) Preferably the gas concentration sensor according to the invention is further characterized in that the sensor is used for measurement of gas concentration within an intake pipe or canister purge line of an internal combustion engine.

The gas concentration sensor according to the present invention can measure concentration of a gas (vaporized fuel) which flows through, for example, an intake pipe or canister purge line.

Accordingly, the gas concentration sensor of the present invention can be used for optimal control of the ratio between fuel and air supplied to the internal combustion engine.

The following example method may be employed for such control. The concentration of a gas within the intake pipe or canister purge line is measured by use of the gas concentration sensor of the present invention; the flow rate of the gas is measured by another method; and the quantity of vaporized fuel supplied from the intake pipe to the internal combustion engine (hereinafter referred to as "vaporized-fuel quantity") is calculated from the gas concentration and the gas flow rate.

Accordingly, the total quantity of fuel supplied to the internal combustion engine can be accurately calculated from the vaporized-fuel quantity and a known quantity of fuel supplied from an injector to the internal combustion engine; and on the basis of the total quantity, the fuel/air ratio within a gas which takes part in combustion within the internal combustion engine can be controlled properly. As a result, toxic components contained in exhaust gas can be reduced in concentration.

Figure 1:
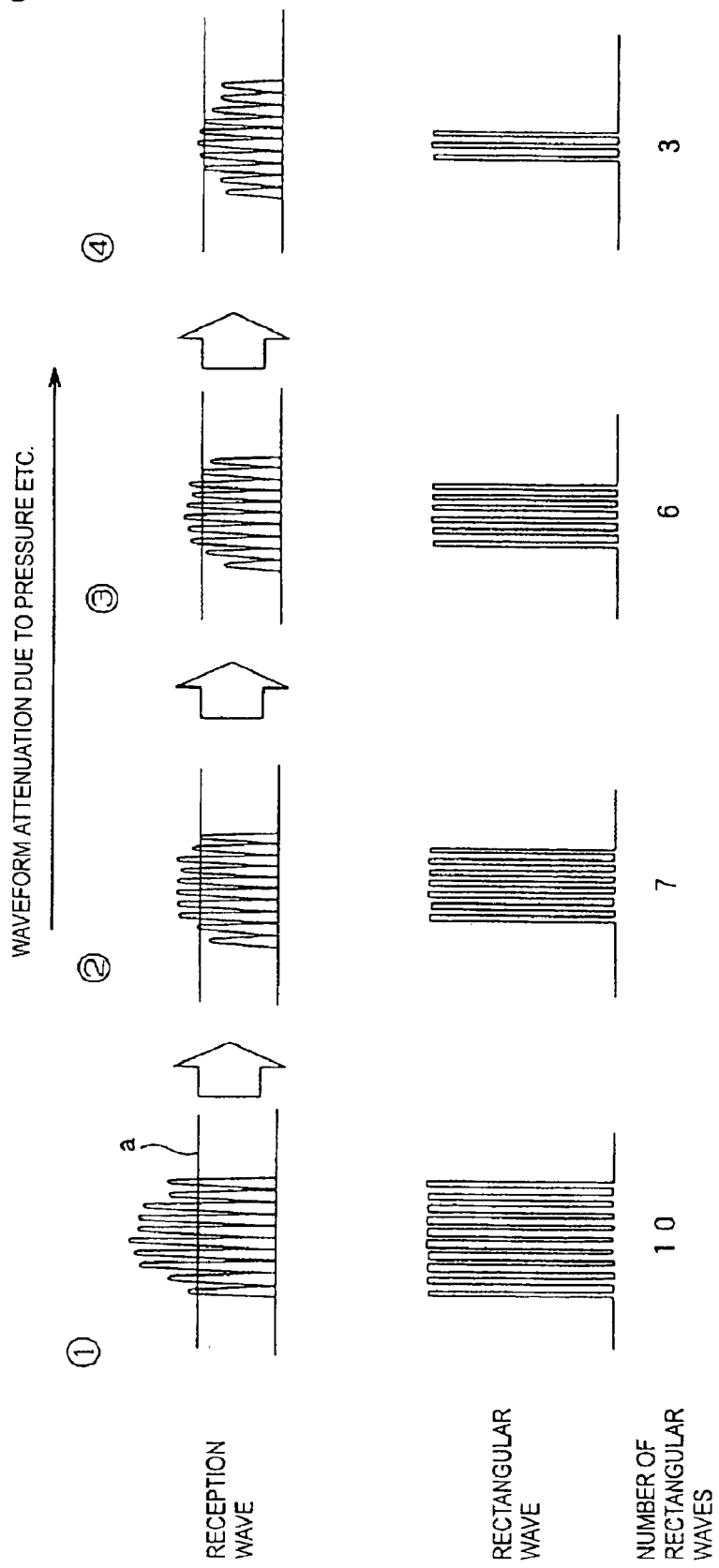
FIG. 1 is an explanatory diagram showing a method of generating rectangular waves on the basis of reception waves.
Figure 2:
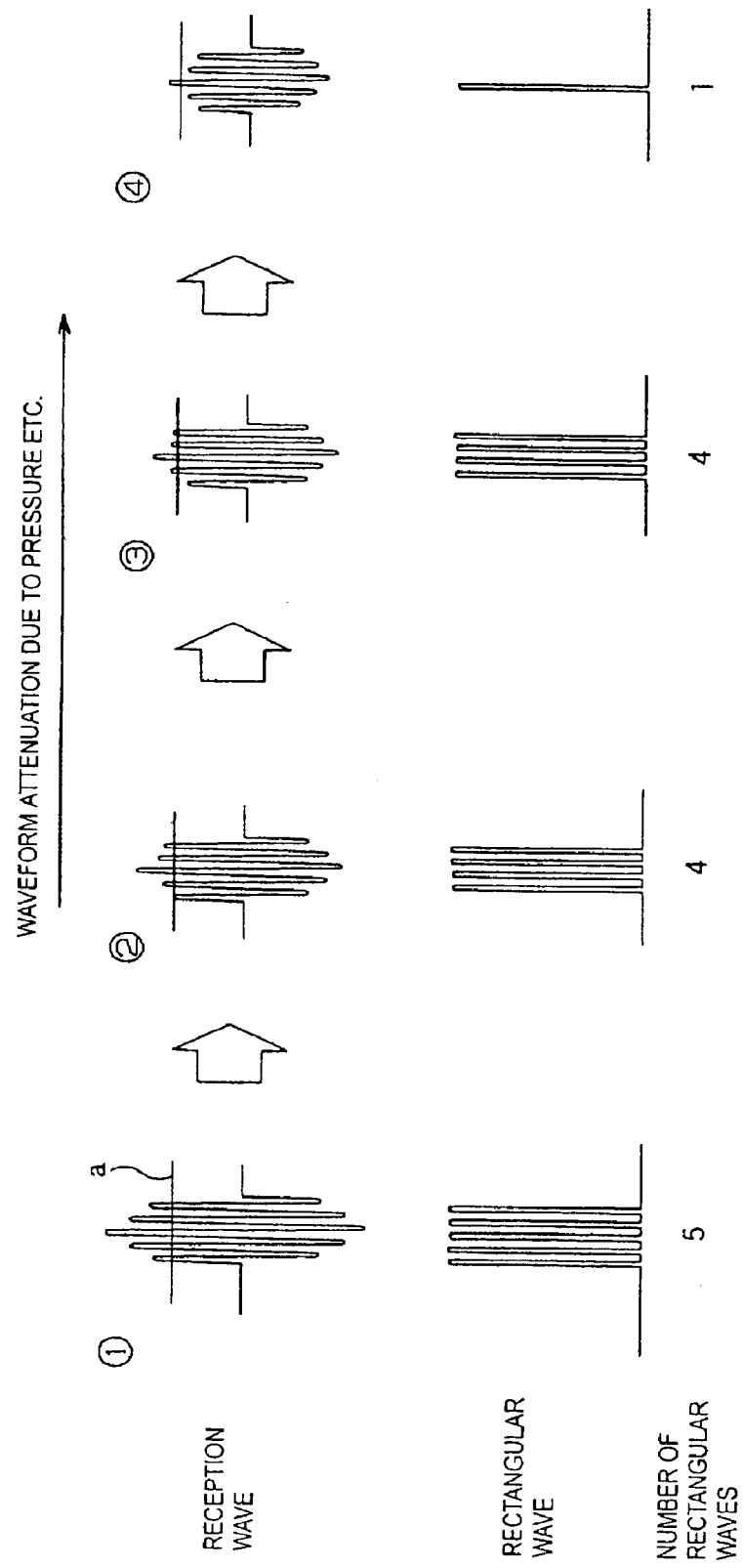
FIG. 2 is an explanatory diagram showing a method of generating rectangular waves on the basis of reception waves.

Reference numerals are used to identify items shown in the drawings as follows:

1 gas concentration sensor
3 drive/calculation circuit
5 ultrasonic-wave transmission/reception element (ultrasonic element)
7 measurement chamber
9 reflection surface
11 thermistor

DESCRIPTION OF THE PREFERRED EMBODIMENTS

Embodiments of the invention will now be described, by way of example only, with reference to the accompanying drawings. However, the present invention should not be construed as being limited thereto.

A first embodiment is directed to detection of the concentration of a specific gas (vaporized fuel) in air, which is a gas under measurement (i.e., atmosphere to be measured), by use of a gas concentration sensor utilizing the ultrasonic-wave propagation-time measuring method.

a) First, the structure of the gas concentration sensor according to the present embodiment will be described.

The gas concentration sensor of the present embodiment is an ultrasonic-type gas concentration sensor in which ultrasonic waves are generated by use of a piezoelectric element; in particular, a common ultrasonic-wave transmission/reception element (hereinafter may be referred to as simply an "ultrasonic element") is used for transmission and reception of ultrasonic waves.

Figure 3:
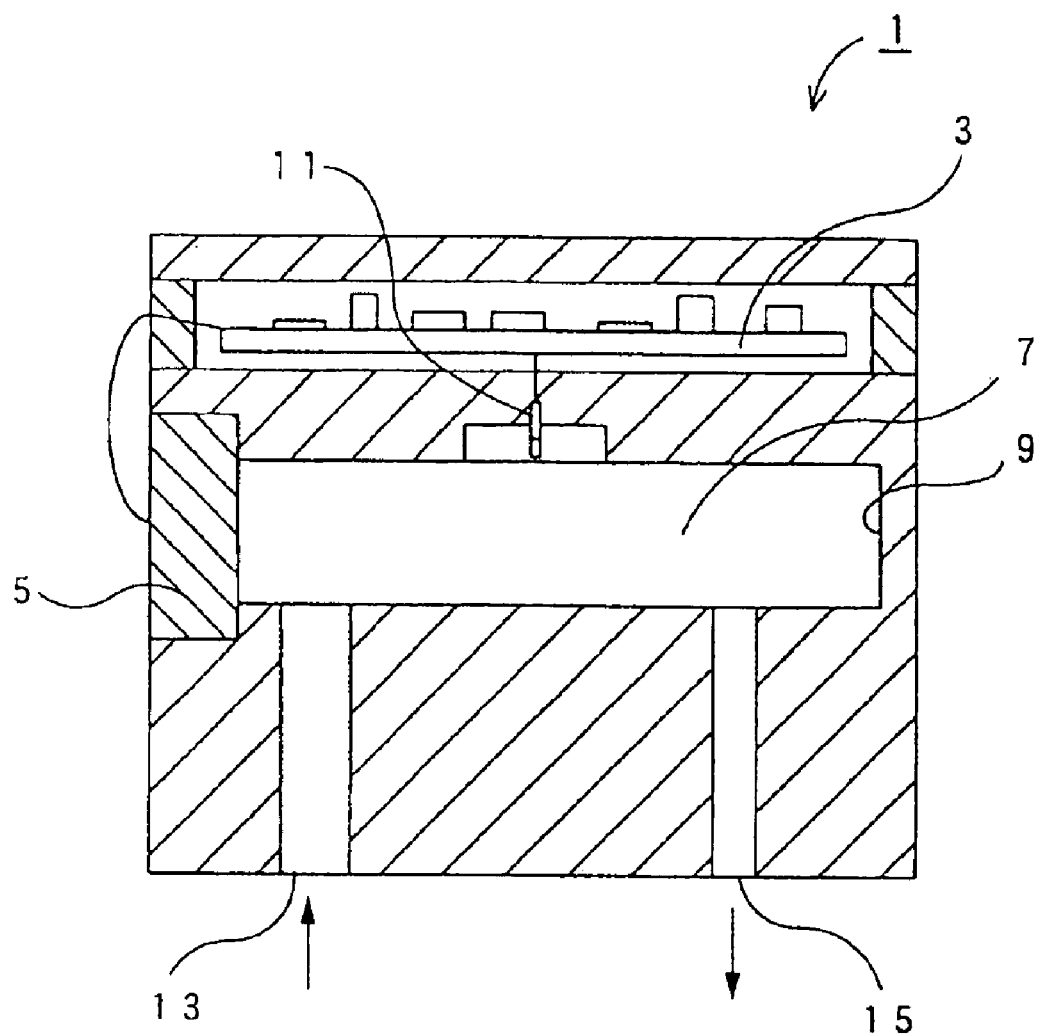
FIG. 3 is an explanatory view showing a gas concentration sensor embodying the invention.

Specifically, as shown in FIG. 3, the gas concentration sensor 1 comprises a drive/calculation circuit 3 for performing drive and calculation required for detection of gas concentration; an ultrasonic element 5 for effecting transmission and reception of ultrasonic waves; a measurement chamber 7 into which is introduced intake gas, which is a gas under measurement and contains a specific gas; a reflection surface 9 which is separated a predetermined distance from the ultrasonic element 5 such that the reflection surface 9 faces the ultrasonic element 5 to thereby reflect ultrasonic waves within the measurement chamber 7; a thermistor 11 for measuring the temperature within the measurement chamber 7; a gas inlet port 13 into which intake gas flows; and a gas outlet port 15 through which the intake gas exits.

b) The principle of operation of the gas concentration sensor 1 will next be described with reference to FIG. 4.

Figure 4:
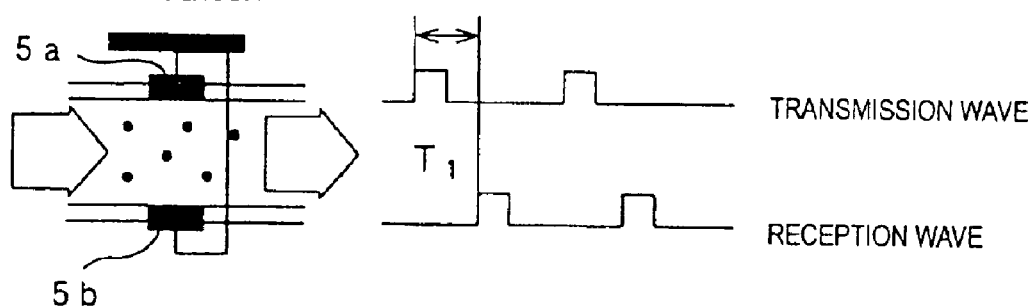
FIGS. 4(a) and 4(b) are an explanatory views showing the basic principle of the gas concentration sensor of the embodiment.
Figure 4:
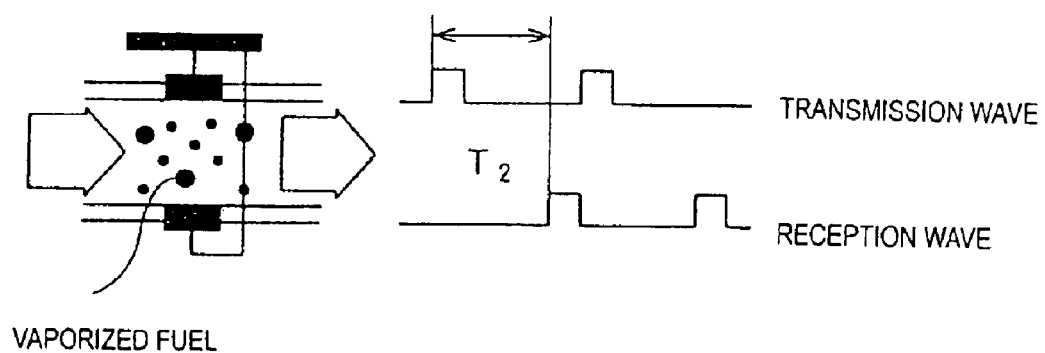

In FIG. 4, in order to facilitate understanding, the ultrasonic element 5 is illustrated as having separate transmission and reception elements 5a and 5b. However, in the present embodiment, the ultrasonic element 5 actually has a common transmission/reception element.

(1) As shown in FIG. 4, when concentration measurement is performed by use of the gas concentration sensor 1, an ultrasonic wave is transmitted from the transmission device 5a, and the ultrasonic wave is received by the reception device 5b. At this time, a shift is produced between the transmission wave and the reception wave in accordance with a propagation time which varies with concentration of a specific gas (e.g., vaporized fuel) within the intake gas.

When the concentration of vaporized fuel is low, as in FIG. 4(a), a relatively short propagation time $T_1$ results; i.e., a relatively small shift is produced between the transmission wave and the reception wave. In contrast, when the concentration of vaporized fuel is high, as shown in FIG. 4(b), a relatively long propagation time $T_2$ results; i.e., a relatively large shift is produced between the transmission wave and the reception wave. Accordingly, the gas concentration can be determined by detecting a sensor output which corresponds to the propagation time.

(2) Next, general operation of the gas concentration sensor 1 which operates on the basis of the above-described principle will be described.

A gas under measurement flows from the gas inlet port 13 into the measurement chamber 7 and then flows to the outside through the gas outlet port 15. During such flow, the concentration of a specific gas contained in the gas under measurement is measured within the measurement chamber 7. Specifically, when the propagation time of an ultrasonic wave within the measurement chamber 7 is measured, an ultrasonic wave is first transmitted from the ultrasonic element 5. The transmitted ultrasonic wave passes through the gas under measurement and is reflected by the reflection surface 9. The reflected wave passes through the gas under measurement and is received by the same ultrasonic element 5.

As will be described in detail below, the drive/calculation circuit 3 calculates the propagation time between the timing of transmission (emission time) of a transmission wave and the timing of reception (arrival time) of a corresponding reception wave. The drive/calculation circuit 3 also detects the temperature within the measurement chamber 7 on the basis of a signal from the thermistor 11.

Since the propagation time depends on gas concentration and is affected by temperature, the drive/calculation circuit 3 obtains the concentration of a specific gas from a predetermined map and in accordance with a procedure which will be described below.

c) Next, the procedure for detection of gas concentration will be described in more detail, together with processing performed in the drive/calculation circuit 3. It is to be noted that in FIG. 5 the internal structure of a microprocessor 21 is shown functionally.

Figure 5:
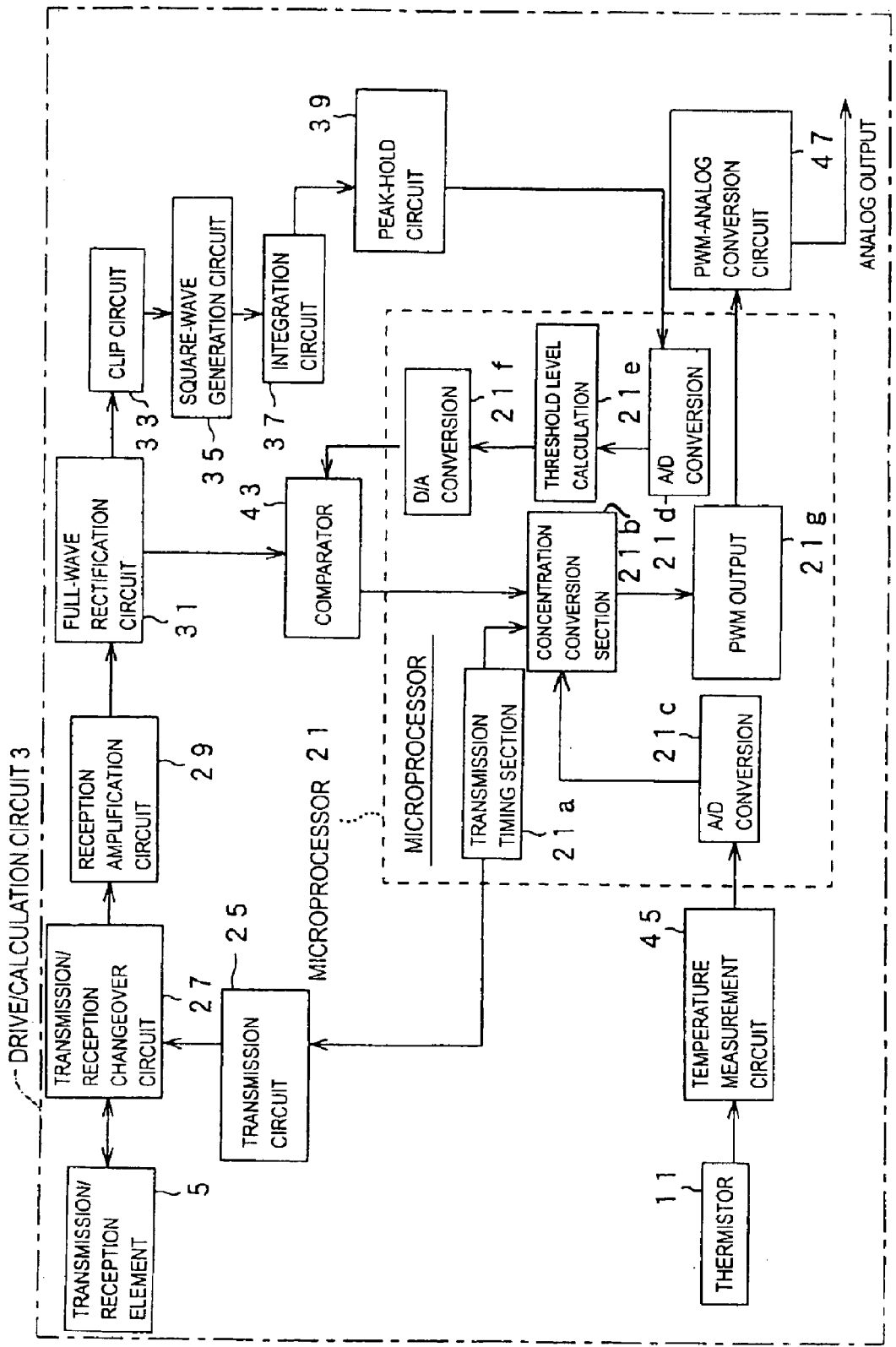
FIG. 5 is a block diagram showing the electrical configuration of the gas concentration sensor of the embodiment.

(i) As shown in the block diagram of FIG. 5, a transmission timing section 21a of the microprocessor 21 produces a signal indicating a transmission timing, which is sent to a transmission circuit 25. An electrical pulse signal output from the transmission circuit 25 is transmitted to the ultrasonic element 5 via a transmission/reception changeover circuit 27. The ultrasonic element 5 converts the electrical pulse signal to an ultrasonic wave (transmission wave) and transmits it toward the reflection surface 9.

Pulse energy (a reception wave) received by the ultrasonic element 5 after being reflected by the reflection surface 9 is converted to an electrical signal by the ultrasonic element 5.

At this point of time, the transmission/reception changeover circuit 27 switches the signal path from the transmission circuit 25 to a reception amplification circuit 29. Therefore, after being amplified by the reception amplification circuit 29, the electrical signal (indicating the reception wave) from the ultrasonic element 5 is fed to a full-wave rectification circuit 31 so as to undergo full-wave rectification. Subsequently, noise is removed from the resultant signal by a clip circuit 33.

Subsequently, a rectangular-wave generation circuit 35 generates rectangular waves corresponding to the electric signal (which represents the reception signal). That is, the rectangular-wave generation circuit 35 generates rectangular waves which are equal in number to pulses which are contained in the electric signal and which have an amplitude greater than the predetermined value a.

An integration circuit 37 integrates the rectangular waves to thereby obtain an integral value, and a peak-hold circuit 39 holds a peak value of the integral value.

Subsequently, an A/D conversion section 21d converts the peak value to a digital signal, which is then amplified at a proper amplification factor by a threshold-level calculation section 21e in order to obtain a threshold level.

A D/A conversion section 21f converts the thus-obtained threshold level to an analog signal, which is fed to a comparator 43.

The comparator 43 judges whether the electric signal obtained through full-wave rectification of a reception signal performed in the full-wave rectification circuit 31 has reached the threshold level.

Figure 6:
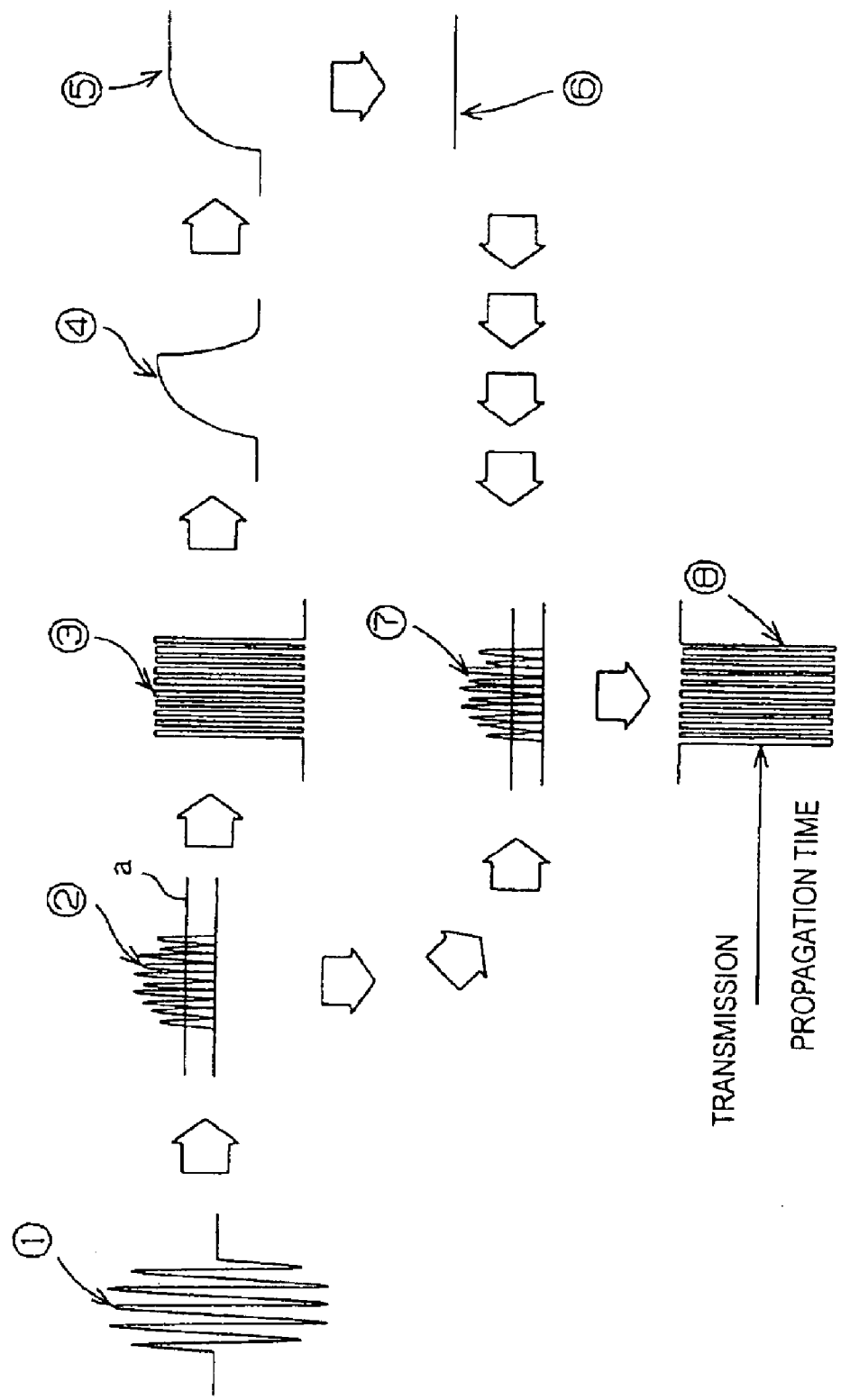
FIG. 6 is an explanatory view showing processing of a reception wave in the embodiment.

(ii) FIG. 6 shows variations in the reception wave up to this point. The reception wave is amplified by the reception amplification circuit 29 ((1) in FIG. 6), subjected to full-wave rectification performed by the full-wave rectification circuit 31 ((2) in FIG. 6), and subjected to noise cut performed by the clip circuit 33. Subsequently, rectangular waves ((3) in FIG. 6) corresponding to the reception wave having undergone full-wave rectification (full-wave-rectified wave) are generated by the rectangular-wave generation circuit 35. The rectangular waves are integrated by the integration circuit 37 ((4) in FIG. 6). On the basis of a resultant integral value, the peak-hold circuit 39 holds a peak value ((5) in FIG. 6), which is used for calculation of a threshold level. On the basis of the peak value, the threshold-level calculation section 21e sets a threshold level ((6) in FIG. 6), which is used by the comparator 43 in order to judge whether a reception wave has arrived.

That is, the comparator 43 compares the threshold level and the full-wave-rectified wave shown at (2) in FIG. 6 (as shown at (7) in FIG. 6). When a first one of the pulses which are contained in the full-wave-rectified wave and have an amplitude greater than the threshold level is detected, the reception wave is judged to have arrived ((8) in FIG. 6).

(iii) Referring back to FIG. 5, when the comparator 43 judges that the reception wave has arrived, a signal for reporting the same is transmitted to a concentration conversion section 21b of the microprocessor 21.

The time of reception of the above signal is a reception timing (arrival time). It is to be noted that the transmission timing (emission time) is transmitted in advance from the transmission timing section 21a to the concentration conversion section 21b and stored therein.

Upon reception of the signal from the comparator 43, the concentration conversion section 21b of the microprocessor 21 calculates a period of time (i.e., propagation time) from the emission time to the arrival time.

(iv) Meanwhile, the signal from the thermistor 11 is input to an A/D conversion section 21c via a temperature measurement circuit 45, and a signal representing the temperature is input to the concentration conversion section 21b.

(v) Accordingly, the concentration conversion section 21b obtains the concentration of the specific gas from the propagation time, while taking the temperature conditions into consideration.

More specifically, a sonic velocity C is first calculated from the propagation time by use of the following equation (1):

$$\text{Sonic velocity } C = (\text{round-trip distance between the element surface and the reflection surface})/\text{propagation time} \quad (1)$$

Figure 7:
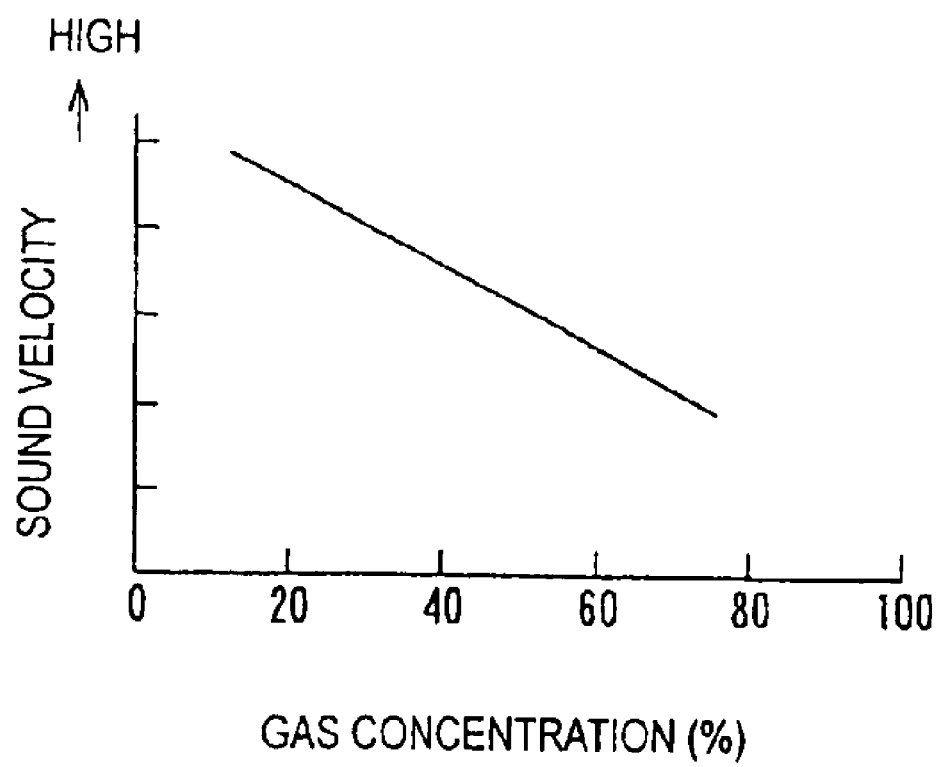
FIG. 7 is a graph showing a map for obtaining gas concentration which is used in the embodiment.

Next, since the sonic velocity C varies with temperature, through use of the measured temperature, the sonic velocity C is converted to a sonic velocity KC measured at a reference temperature. Subsequently, gas concentration is obtained by use of a map (e.g., a map as shown in FIG. 7) which shows the relationship (proportional relationship) between sonic velocity KC and gas concentration.

Subsequently, a signal representing the gas concentration is fed via a PWM output section 21g to a PWM analog conversion circuit 47, at which the signal representing the gas concentration is converted to an analog value in order to provide an analog output.

As described above, in the present embodiment, a threshold level is set on the basis of an integral value of a reception wave (full-wave-rectified wave); during measurement of propagation time, a period of time between the timing of transmission of a transmission wave and a time when a reception wave (full-wave-rectified wave) attains the threshold level is measured as a propagation time; and gas concentration is detected on the basis of the propagation time and in consideration of temperature. Therefore, the detection is hardly affected by a decrease in pressure of atmospheric air (gas under measurement), and thus the gas concentration can be detected accurately at all times.

That is, in the conventional technique (fixed threshold level), when the pressure of a gas under measurement decreases, a reception wave attenuates, and a time which the reception wave requires to attain the threshold level increases, resulting in an increase in propagation time, thereby rendering measurement of gas concentration inaccurate. By contrast, in the measurement method according to the present embodiment, even when the reception wave attenuates, measurement of propagation time; i.e., measurement of gas concentration, can be performed accurately, because the threshold level is set on the basis of the reception wave (full-wave-rectified wave).

In particular, in the present embodiment, since the full-wave-rectified wave is used for setting of the threshold level, the threshold level changes to accurately follow attenuation of the reception wave.

That is, since rectangular waves are generated on the basis of the full-wave-rectified wave including a greater number of pulses in total, the number of rectangular waves decreases to accurately follow attenuation of the full-wave-rectified wave, and the threshold level (which is set on the basis of an integral value of the rectangular waves) also decreases to accurately follow attenuation of the full-wave-rectified wave.

Therefore, the gas concentration sensor 1 according to the present embodiment can always perform accurate measurement of propagation time, while further eliminating the influence of pressure drop of the atmosphere (gas under measurement), thereby enabling accurate measurement of gas concentration.

Further, the present embodiment employs a method which detects, as an arrival time, a point in time when the full-wave-rectified wave has reached the threshold level.

Therefore, it becomes possible to eliminate the necessity of integrating reception waves, which is required in a method in which a reception wave is integrated to obtain an integral value, and a point in time when the integral value has reached the reference value is measured as an arrival time. Thus, calculation processing and apparatus configuration can be simplified.

d) Next will be described an evaluation test performed in order to confirm the effects of the gas concentration sensor 1 of the present embodiment.

Figure 8:
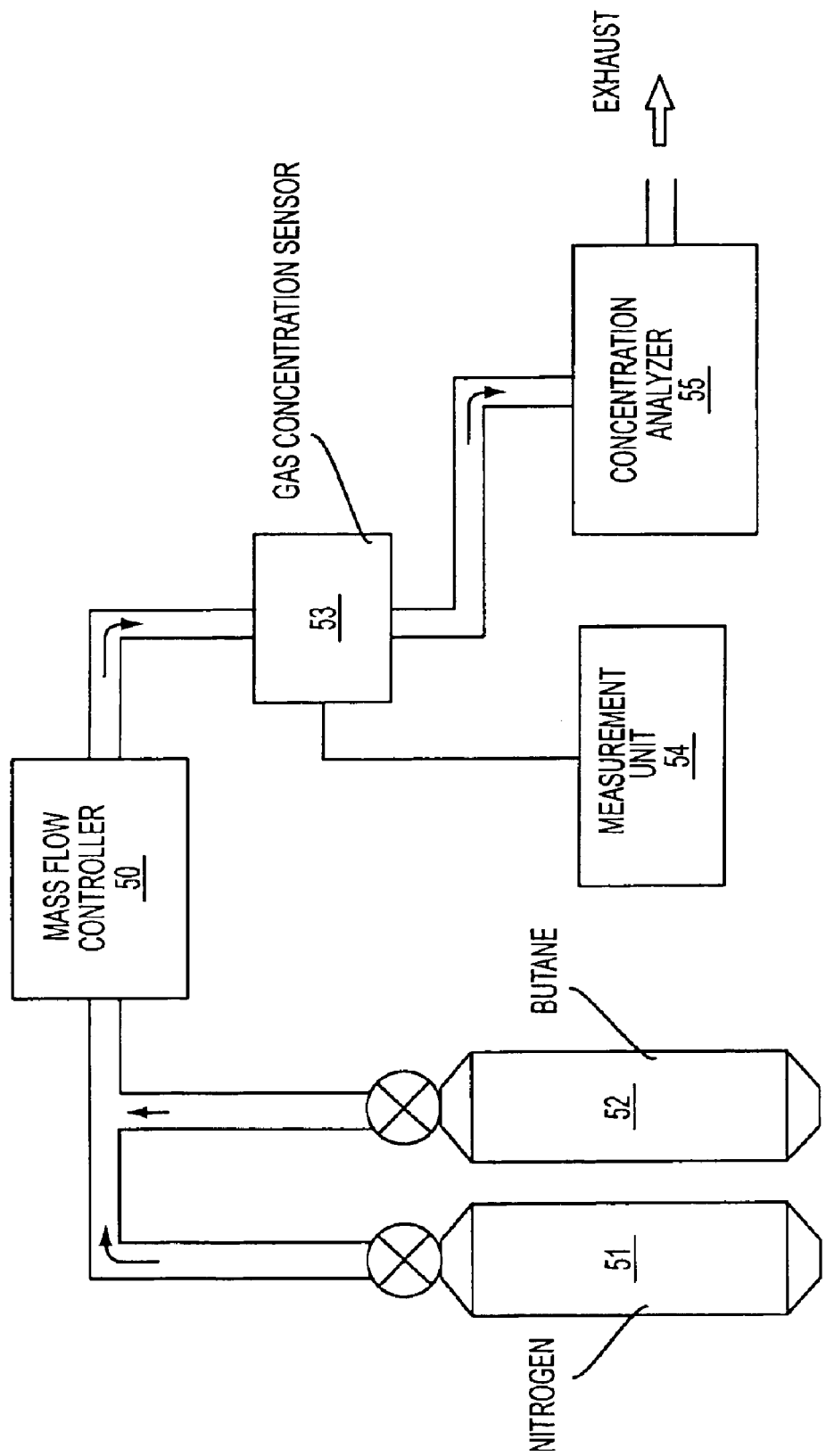
FIG. 8 is an explanatory view showing an apparatus for evaluating the gas concentration sensor in the embodiment.

(1) An evaluation apparatus as shown in FIG. 8 was used for the evaluation test. The evaluation apparatus comprises a mass flow controller 50 for adjusting gas flow rate; nitrogen source 51 and butane source 52; a gas concentration sensor 53 to be evaluated; a measurement unit 54 (display unit) for displaying measurement value output from the gas concentration sensor; and a concentration analyzer 55 (e.g., an infrared concentration analyzer) for confirming concentration.

The following measurement was performed. While the pressure of the gas mixture was varied, propagation time at the time of gas-concentration detection was measured at 25° C., and a propagation time variation ratio was calculated. The term "propagation time variation ratio" refers to percent variation in propagation time from a theoretical value.

Figure 9:
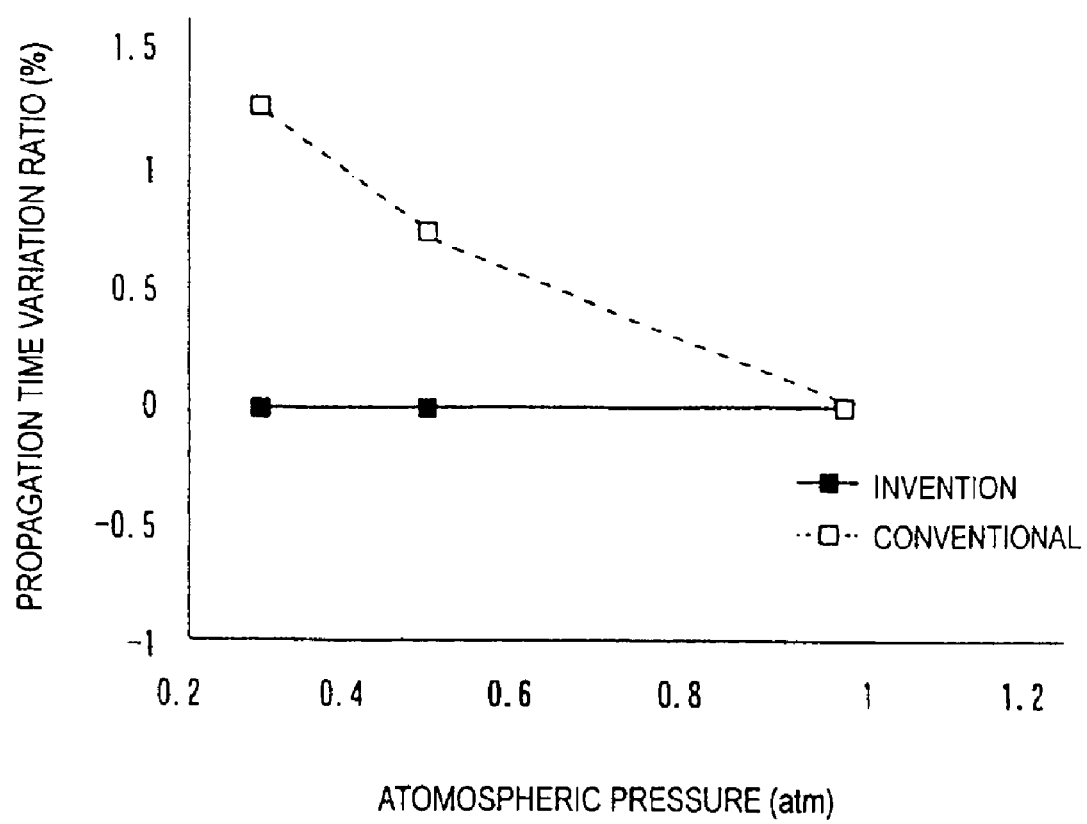
FIG. 9 is a graph relating to the embodiment and showing a ratio of variation in propagation time when the atmospheric pressure is changed.

The results are shown in FIG. 9. In the conventional gas concentration sensor, errors involved in propagation time increase as atmospheric pressure decreases. By contrast, in the gas concentration sensor of the present embodiment, errors are hardly produced even when atmospheric pressure changes.

Similar results are obtained even when the ultrasonic element is composed of separate transmission and reception elements.

The present invention is not limited to the above-described embodiment and may be practiced in various forms without departing from the gist of the present invention.

For example, the above-described embodiment may be modified in such a manner that, instead of a reception wave having undergone full-wave rectification (full-wave-rectified wave), a reception wave (not having been subjected to full-wave rectification) is compared with the threshold level by means of the comparator 43.

Further, the above-described embodiment may be modified in such a manner that an integral value of a reception wave or full-wave-rectified wave (or an integral value of a portion of a reception wave or full-wave-rectified wave) is compared with the threshold level by means of the comparator 43.

In this case, the integral value calculated by the integration circuit 37 of FIG. 5 is fed not only to the peak-hold circuit 39, but also to the comparator 43, at which the integral value is compared with the threshold level fed from the D/A conversion section 21f; and a point in time when the integral value has exceeded the threshold level is detected as an arrival time.

This application is based on Japanese Patent Application No. 2001-41680 filed Feb. 19, 2001, the disclosure of which is incorporated herein by reference in its entirety.

What is claimed is:

1. An ultrasonic-wave propagation-time measuring method in which an ultrasonic wave is transmitted by use of an ultrasonic element, a reflection wave of the transmission wave is received as a reception wave by use of the same ultrasonic element or a different ultrasonic element, and a period of time between transmission of the ultrasonic wave and reception of the reception wave is measured as a propagation time, the method comprising:

a reference-value setting step which comprises subjecting a reception wave to full-wave rectification to obtain a full-wave-rectified wave, integrating the full-wave-rectified wave or a portion thereof in order to obtain an integral value, and setting a reference value on the basis of the integral value; and a propagation time measurement step which comprises determining an arrival time of the reception wave by use of the reference value when the propagation time is measured.

2. The ultrasonic-wave propagation-time measuring method as claimed in claim 1, which comprises measuring a point in time when the reception wave or the full-wave-rectified wave has reached the reference valve to thereby determine an arrival time in the propagation time measurement step.

3. The ultrasonic-wave propagation-time measuring method as claimed in claim 1, which comprises integrating the reception wave or full-wave-rectified wave or a portion thereof to obtain an integral value, and measuring a point in time when the integral value has reached the reference value as an arrival time in the propagation time measurement step.

4. A gas concentration sensor which utilizes the ultrasonic-wave propagation-time measuring method as claimed in claim 1.

5. A gas concentration sensor which utilizes the ultrasonic-wave propagation-time measuring method as claimed in claim 2.

6. A gas concentration sensor which utilizes the ultrasonic-wave propagation-time measuring method as claimed in claim 3.

7. The gas concentration sensor as claimed in claim 4, wherein the sensor is used for measurement of gas concentration within an intake pipe or canister purge line of an internal combustion engine.

8. The gas concentration sensor as claimed in claim 5, wherein the sensor is used for measurement of gas concentration within an intake pipe or canister purge line of an internal combustion engine.

9. The gas concentration sensor as claimed in claim 6, wherein the sensor is used for measurement of gas concentration within an intake pipe or canister purge line of an internal combustion engine.

* * * * *